United States Patent
Denker et al.

(10) Patent No.: US 6,907,285 B2
(45) Date of Patent: Jun. 14, 2005

(54) IMPLANTABLE DEFIBRILLARTOR WITH WIRELESS VASCULAR STENT ELECTRODES

(75) Inventors: Stephen Denker, Mequon, WI (US); Cherik Bulkes, Sussex (GB); Arthur J. Beutler, Greendale, WI (US)

(73) Assignee: Kenergy, Inc., Mequon, WI (US)

( * ) Notice: Subject to any disclaimer, the term of this patent is extended or adjusted under 35 U.S.C. 154(b) by 377 days.

(21) Appl. No.: 10/197,191

(22) Filed: Jul. 17, 2002

(65) Prior Publication Data

US 2002/0183791 A1 Dec. 5, 2002

Related U.S. Application Data

(63) Continuation-in-part of application No. 09/760,936, filed on Jan. 16, 2001, now Pat. No. 6,445,953.

(51) Int. Cl.[7] ............................................. A61N 1/39
(52) U.S. Cl. .......................... 607/5; 607/37; 607/116; 607/126; 607/33
(58) Field of Search ............................... 607/5, 32, 33, 607/37, 60, 61, 116, 119, 122, 123, 125, 130, 149, 126; 600/375

(56) References Cited

U.S. PATENT DOCUMENTS

| | | | |
|---|---|---|---|
| 452,774 A | | 5/1891 | Dickey |
| 3,952,750 A | * | 4/1976 | Mirowski et al. ............... 607/5 |
| 5,170,802 A | | 12/1992 | Mehra |
| 5,224,491 A | | 7/1993 | Mehra |
| 5,411,535 A | | 5/1995 | Fujii et al. |
| 5,423,865 A | * | 6/1995 | Bowald et al. ................. 507/5 |
| 5,531,779 A | | 7/1996 | Dahl et al. |
| 5,649,952 A | | 7/1997 | Lam |
| 5,674,249 A | * | 10/1997 | de Coriolis et al. ............ 607/5 |
| 5,755,737 A | * | 5/1998 | Prieve et al. ................... 607/4 |
| 5,800,535 A | | 9/1998 | Howard, III |
| 5,814,089 A | | 9/1998 | Stokes et al. |
| 5,954,761 A | | 9/1999 | Machek et al. |
| 5,999,851 A | * | 12/1999 | White ........................... 60/75 |
| 6,015,387 A | * | 1/2000 | Schwartz et al. ........... 600/504 |
| 6,061,596 A | | 5/2000 | Richmond et al. |
| 6,141,588 A | | 10/2000 | Cox et al. |
| 6,164,284 A | | 12/2000 | Schulman et al. |
| 2001/0053925 A1 | | 12/2001 | Whitehurst |
| 2002/0026228 A1 | * | 2/2002 | Schauerte .................... 607/122 |

FOREIGN PATENT DOCUMENTS

WO    WO 00/30534    6/2000

* cited by examiner

*Primary Examiner*—Kennedy Schaetzle
(74) *Attorney, Agent, or Firm*—George E. Haas; Quarles & Brady LLP

(57) ABSTRACT

A cardiac defibrillator includes a fibrillation detector, which determines when a medical patient requires defibrillation at which time a transmitter produces a radio frequency signal. A first stent electrode is implanted into a blood vessel at a first location in the medical patient and a second stent electrode is implanted into a blood vessel at a second location. The first stent electrode contains an electronic circuit that is electrically connected to the second stent electrode. In response to receiving the radio frequency signal, the electronic circuit uses energy from that signal to apply an electric defibrillation pulse between the first and second stent electrodes.

12 Claims, 2 Drawing Sheets

FIG. 5
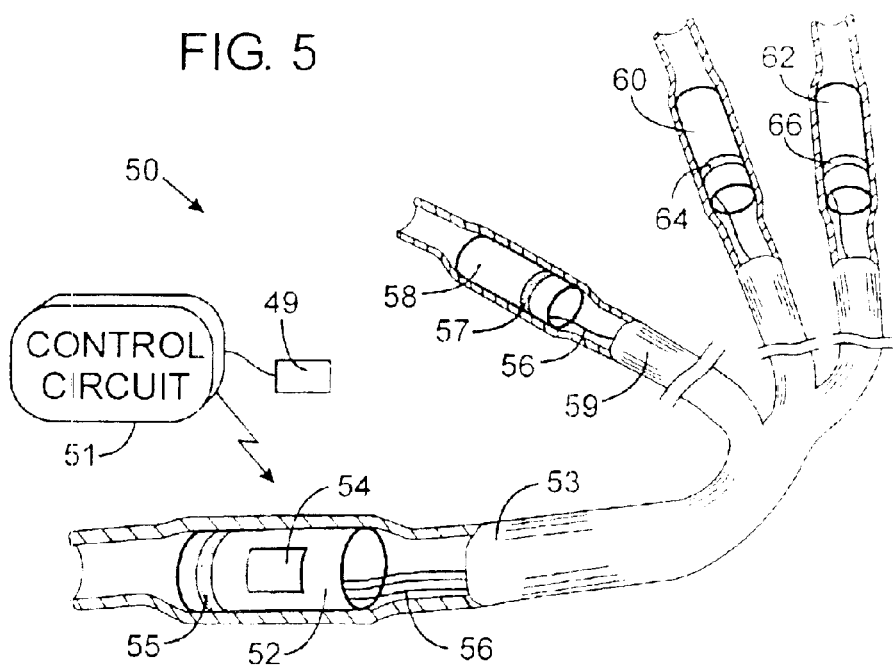
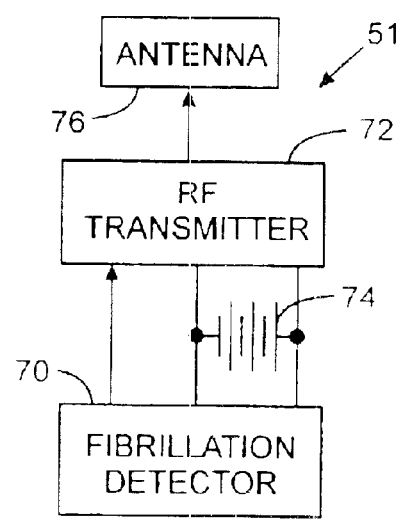
FIG. 6
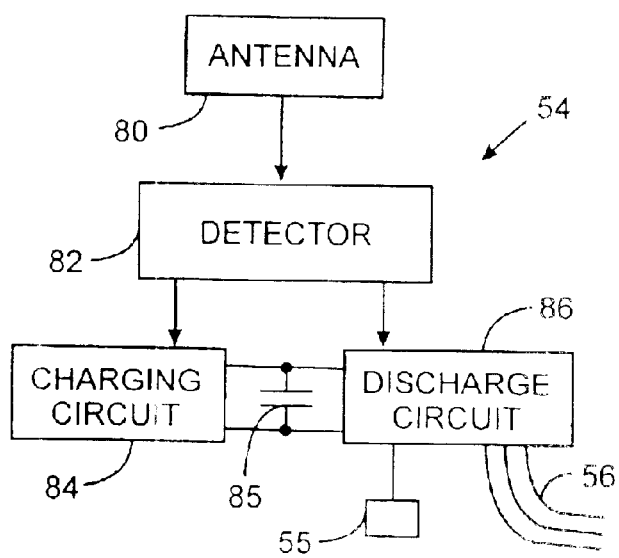
FIG. 7

IMPLANTABLE DEFIBRILLARTOR WITH WIRELESS VASCULAR STENT ELECTRODES

CROSS-REFERENCE TO RELATED APPLICATIONS

This application is a continuation-in-part of U.S. patent application Ser. No. 09/760,936 filed Jan. 16, 2001, now U.S. Pat. No. 6,445,953.

STATEMENT REGARDING FEDERALLY SPONSORED RESEARCH OR DEVELOPMENT

Not Applicable

BACKGROUND OF THE INVENTION

1. Field of the Invention

The present invention relates to implantable medical devices which deliver energy to cardiac tissue for the purpose of maintaining or producing a regular heart rate. Such devices are commonly referred to as cardiac pacing devices and defibrillators.

2. Description of the Related Art

A remedy for people with slowed or disrupted natural heart beating is to implant a cardiac pacing device. A cardiac pacing device is a small electronic apparatus that stimulates the heart to beat at regular rates. It consists of a pulse generator, implanted in the patient's chest, which produces electrical pulses to stimulate heart contractions. Electrical leads extend from the pulse generator to electrodes placed adjacent to specific muscles of the heart, which when electrically stimulated produce contraction of the adjacent heart chambers.

Modern cardiac pacing devices adapt their pulse rate to adjust the heartbeats to the patient's level of activity, thereby mimicking the heart's natural beating. The pulse generator modifies that rate by tracking the activity at the sinus node of the heart or by responding to other sensors that monitor body motion and rate of breathing.

Different pacing needs are met by adjusting the programming of the pulse generator and by the location of the electrodes. It is quite common that the leads extend through blood vessels which enter the heart so that the electrodes can be placed in the muscle of the heart chamber requiring stimulation. This requires that the leads extend for some distance through the blood vessels and may necessitate that the leads pass through one or two heart valves. In other patients, patch electrodes are placed on the exterior heart surface with wires extending through tissue to the pacing device. With either type of lead placement, it is important that the electrodes be attached to the proper positions on the heart to stimulate the muscles and produce contractions. Thus it is desirable to properly locate the electrodes for maximum heart stimulation with minimal adverse impact to other physiological functions, such as blood circulation.

Other patients have hearts that occasionally go into fibrillation where the heart has very rapid shallow contractions and, in the case of ventricular fibrillation, may not pump a sufficient amount of blood to sustain life. Administration of a controlled electrical shock to the heart often is required to restore a normal rhythm. A defibrillator often is implanted in the chest cavity of a person who is susceptible to reoccurring episodes of ventricular fibrillation. Similar to a pacing device, the implanted defibrillator senses the rapid heart rate during fibrillation and applies a relatively high energy electrical pulse through wires connected to electrodes attached to the exterior wall of the heart. The defibrillator generates a much more intense electrical pulse than is used by pacing devices which merely stimulate contractions of the heart.

SUMMARY OF THE INVENTION cardiac defibrillator includes a control circuit that has a fibrillation detector, which determines when a medical patient requires defibrillation. A transmitter produces a radio frequency signal at a given frequency in response to the fibrillation detector determining that defibrillation is required. A first stent electrode and a second electrode are provided for implantation into blood vessels at different locations in the medical patient. For example, the first stent electrode and a second electrode are to be implanted on different sides of the patient's heart.

An electronic circuit is mounted to the first stent electrode and electrically connected to the second stent electrode. Upon receipt of the radio frequency signal, the electronic circuit applies an electric defibrillation pulse between the first stent electrode and the second stent electrode.

In the preferred embodiment, the electronic circuit contains an RF detector that is tuned to receive the radio frequency signal. A charging circuit employs energy from the radio frequency signal received by the RF detector to charge a capacitor which acts as an electrical storage device. A discharge circuit responds to the control signal by applying the stored energy from the capacitor to the first and second stent electrodes, thereby producing a defibrillation pulse across the patient's heart.

BRIEF DESCRIPTION OF THE DRAWINGS

FIG. 5 is a representation of an implanted defibrillator employing vascular stent electrodes;

FIG. 6 is a block diagram of a defibrillator control circuit in FIG. 5; and

FIG. 7 is a block diagram of a defibrillator pulsing circuit on a vascular stent.

DETAILED DESCRIPTION OF THE INVENTION

Figure 1:
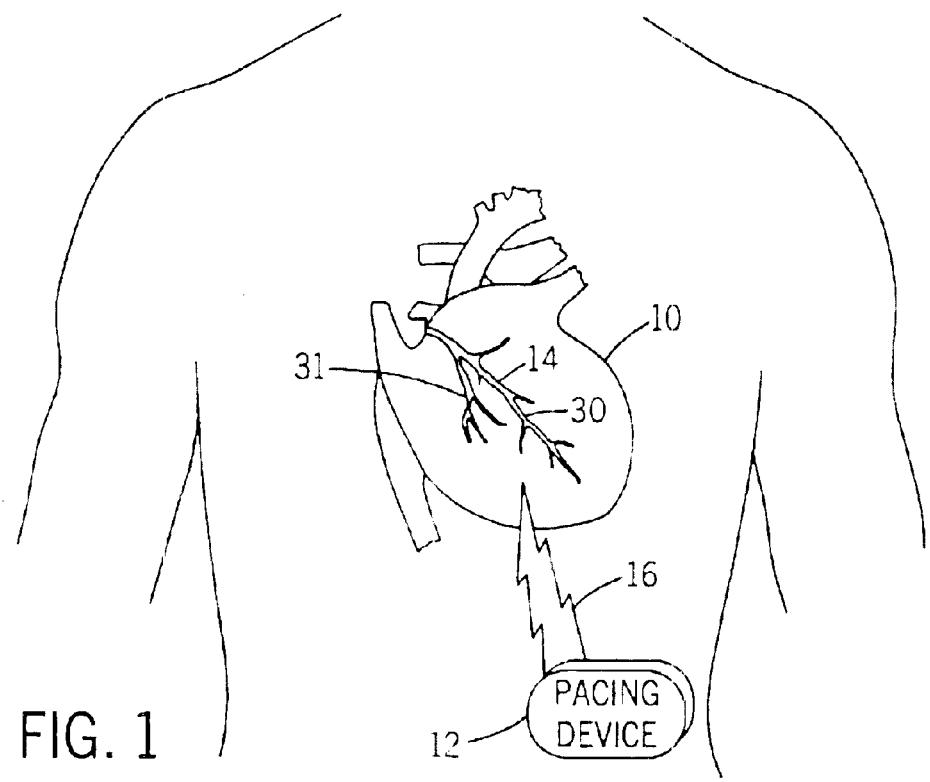
FIG. 1 is a schematic representation of a cardiac pacing device implanted in a medical patient.

With initial reference to FIG. 1, an apparatus for applying electrical stimulation to pace a heart 10 comprises a pacing device 12 and one or more vascular electrode-stents located in arteries 14 which supply blood to the heart muscles. As will be described in greater detail, the pacing device 12 emits a radio frequency signal 16 which produces an electric current in the implanted vascular electrode-stent thereby stimulating the heart muscle.

Figure 2:
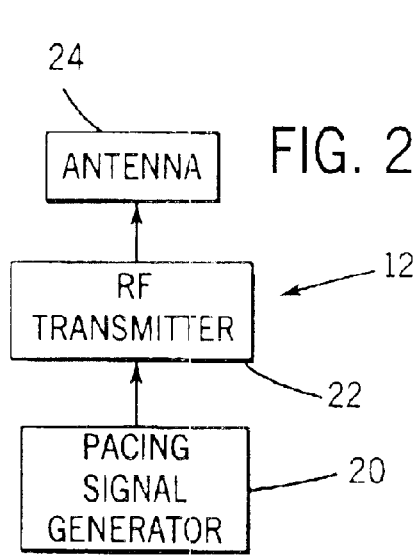
FIG. 2 is a circuit diagram of the pacing device in FIG. 1.

Referring to FIG. 2, the pacing device 12 comprises a conventional pacing signal generator 20 similar to that utilized in previous cardiac pacers that use electrodes connected to leads. The internal circuitry and operation of the pacing signal generator is similar to those prior cardiac pacers. However, instead of the output stimulation signals being applied to the electrodes via leads, the pacing signals are applied to an input of a radio frequency (RF) transmitter 22. Both the pacing signal generator 20 and the RF transmitter 22 are powered by a battery (not shown). In response to the stimulation signal (also known as a pacing signal) from the generator 20, the radio frequency transmitter 22 generates a correspondingly long pulse of the radio frequency signal 16 that is transmitted throughout the chest cavity via an antenna 24. Preferably the antenna 24 either is located relatively close to the heart or is of a type which focuses the radio frequency signal toward the heart.

Figure 3:
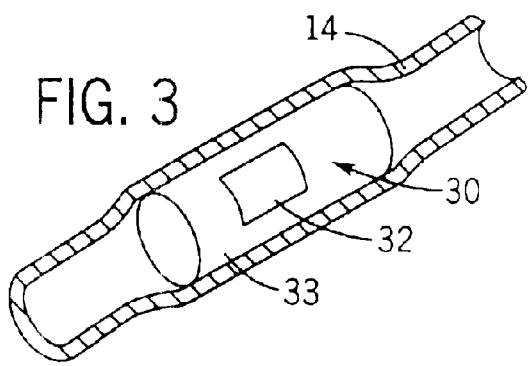
FIG. 3 is an isometric cut-away view of a cardiac blood vessel with a vascular electrode-stent.

FIG. 3 illustrates an electrode-stent 30 that is placed in a blood vessel 14 of the heart 10. The body 33 of the electrode-stent 30 has a design similar to well-known expandable vascular stents that are employed to enlarge a restricted vein or artery. Such vascular stents have a generally tubular design that initially is collapsed to a relatively small diameter enabling them to pass freely through an blood vessel of a patient.

The procedure for implanting the electrode-stent 30 is similar to that used for conventional vascular stents. For example, the balloon at the end of a standard catheter is inserted into the electrode-stent 30 in a collapsed, or reduced diameter, configuration. That assembly then is inserted through an incision in a vein or artery near the skin of a patient and pushed through the vascular system to the appropriate location adjacent the heart 10. Specifically, the electrode-stent 30 ultimately is positioned in a cardiac blood vessel 14 adjacent to a section of the heart muscle where stimulation should be applied. The balloon of the catheter then is inflated to expand the vascular electrode-stent 30, thereby slightly enlarging the blood vessel 14 which embeds the electrode-stent 30 in the wall of the vein or artery, as seen in FIG. 3. This slight enlargement of the blood vessel and the tubular design of the electrode-stent allows blood to flow relatively unimpeded through the device. The balloon is deflated, the catheter is removed from the patient, and the incision is closed. The electrode-stent 30 remains in the blood vessel without any wire connecting an electrode to pacing device 12. Alternatively a self-expanding stent may be utilized.

Figure 4:
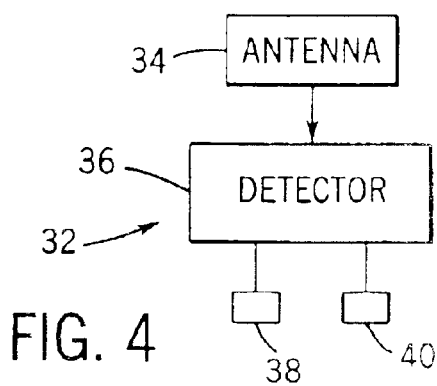
FIG. 4 is a block diagram of an electrical circuit on the vascular electrode-stent.

With reference to FIGS. 3 and 4, the vascular electrode-stent 30 has a body 33 on which is mounted a signal receiving circuit 32. The signal receiving circuit 32 includes an antenna 34, a radio frequency signal detector 36, and a stimulator, that is formed by first and second electrodes 38 and 40, for example. The antenna 34 is connected to an input of the radio frequency signal detector 36. That detector is tuned to the frequency of the RF signal 16 that is emitted by the pacing device 12. Upon detecting the radio frequency signal 16, the detector 36 converts the energy of that signal into an electric current that is applied to the first and second electrodes 38 and 40. Those electrodes form an electric circuit path with the patient's heart tissue allowing for stimulation of that tissue. Thus, each time the pacing device 12 emits a radio frequency signal 16, a pulse of electrical current is produced in the vicinity of the electrode-stent 30, thereby stimulating the heart muscle adjacent to that electrode.

Therefore, instead of coupling the pacing device to the electrodes by wires extending through the vascular system and even the heart itself, the present invention employs radio frequency signals to provide that coupling. This eliminates the need for electrical leads that extend through the blood vessels which can break thus disabling the cardiac pacing. Furthermore, the present electrode-stents 30 and 31 can be located in the cardiac blood vessels 14 at points that are directly associated with the specific muscles requiring stimulation.

With reference to FIG. 1, a plurality of vascular electrode-stents 30 and 31 which are tuned to the same radio frequency can be positioned in cardiac blood vessels at different locations in the heart to provide simultaneous stimulation of the adjacent tissue regions.

Alternatively, the plurality of electrode-stents 30 and 31, implanted in various veins or arteries of the heart muscle, can be tuned to different radio frequencies. In this embodiment, the radio frequency transmitter 22 also is tunable to produce output signals at several different radio frequencies, in response to an electrical control signal from the pacing signal generator 20. The pacing signal generator 20 now specifies the duration and the frequency of the RF signal 16 in order to select an electrode-stent to stimulate the heart muscle at a particular location. As a consequence, different portions of the heart muscle can be stimulated independently and sequentially by varying the radio frequency of the emitted signal 16 to correspond to the frequency to which the electrode-stent 30 in a given location is tuned. Furthermore, the plurality of electrode-stents 30 can be activated in a given sequence by producing a series of pacer signals at different radio frequencies. This enables the pacing device 12 to produce a sequential contraction of the heart chambers to increase cardiac efficiency.

Electrode stents also can be employed with a cardiac defibrillator 50 as illustrated in FIG. 5. The defibrillator 50 has a control circuit 51 which detects fibrillation of the heart via sensor 49 and sends a radio frequency control signal to a primary electrode stent 52 located in a vein or artery 54 in one section of the heart. The primary electrode stent 52 includes the electronic circuitry 54 for the defibrillator 50 and a first electrode 55. The electronic circuitry 54 is connected to a secondary electrode stent 58 by a wire 56 that extends through the vascular system. The secondary electrode stent 58 is located in another blood vessel 59 in a different section of the heart and has a second electrode 57 to which the wire 56 is attached. Additional secondary electrode stents 60 and 62 can be placed into other veins or arteries 59 of the heart. These other secondary electrode stents 60 and 62 have a structure identical to secondary electrode stent 58 with third and fourth electrodes 64 and 66 connected by wires to the primary electrode stent 52. The primary and secondary electrode stents 52, 58, 60 and 62 are implanted using a procedure similar to that described previously for electrode stent 30. The secondary electrode stents 52, 58, 60 and 62 may be significantly smaller that the primary electrode stent 52 as they do not contain electronic circuitry, such as a charge storage capacitor as will be described. Thus the secondary electrode stents can be placed in smaller blood vessels.

With reference to FIG. 6, the defibrillator control circuit 51 preferably is implanted in the chest of the patient, but may be worn externally in close proximity to the heart. The control circuit 51 has a fibrillation detector 70 which employs conventional techniques to detect an irregular heart rate and determine when a defibrillation pulse should be applied to the patient's heart. When that is to occur, the fibrillation detector 70 signals the radio frequency (RF) transmitter 72 to send a wireless signal via antenna 76 to the primary electrode stent 52. The resultant radio frequency signal has greater energy than the signal from the pacing circuit 12 in FIG. 2 and thus provides sufficient energy to enable the primary electrode stent 52 to deliver a more intense defibrillation pulse to the patient. A battery 74 provides power for the control circuit 51.

Referring to FIG. 7, the electronic circuitry 54 on the primary electrode stent 52 includes an antenna 80 for receiving the radio frequency signal from the control circuit 51. An RF detector 82 is tuned to the designated radio frequency and applies energy from the received signal to a charging circuit 84. The charging circuit 84 uses the signal energy to charge a capacitor 85. When the charge on the capacitor is sufficient to produce a defibrillation pulse, a discharge circuit 86 dumps the charge to the electrode 55 on the primary electrode stent 52. The electrodes 57, 64 and 66 of the secondary electrode stents 58, 60 and 62 are connected by wires to the primary electrode stent 52 thereby providing an return pole to complete an electrical circuit for the charge pulse. This action applies an electrical pulse across the first electrode 55 and the second, third and fourth electrodes 57, 64 and 66 which shocks the patient's heart to restore a normal cardiac rhythm. Employing a plurality of secondary electrode stents 58, 60 and 62 to form a circuit to the primary stent provides a greater dispersion of the energy and avoids a local discharge.

The radio frequency signal from the control circuit 51 has a duration that is sufficient to charge the capacitor 85 to the level necessary to deliver the electrical defibrillation pulse. Alternatively, the control circuit 51 may periodically send a brief radio frequency signal to the electronic circuitry 54 on the primary electrode stent 52. This signal does not cause the stent circuitry to deliver a defibrillation pulse, but is used merely to maintain the requisite charge on the capacitor 85. This ensures that the capacitor 85 will be nearly fully charged when a defibrillation pulse is required and shortens the time between receipt of the defibrillation signal and delivery of an electrical pulse to the heart. In this latter case the RF transmitter 72 sends a specially encoded control signal when the patient requires defibrillation. The RF detector 82 responds to that encoded control signal by triggering the discharge circuit 86 to deliver the electrical defibrillation pulse.

The foregoing description was primarily directed to a preferred embodiments of the invention. Even though some attention was given to various alternatives within the scope of the invention, it is anticipated that one skilled in the art will likely realize additional alternatives that are now apparent from disclosure of embodiments of the invention. Accordingly, the scope of the invention should be determined from the following claims and not limited by the above disclosure.

We claim:

1. A cardiac defibrillator, for implantation into a medical patient, comprises:
    a control circuit having a fibrillation detector to determine when the medical patient requires defibrillation, and a transmitter to produce a radio frequency signal at a given frequency in response to the fibrillation detector;
    a first stent electrode for implantation into a blood vessel at a first location in the medical patient;
    a second stent electrode for implantation into a blood vessel at a second location in the medical patient; and
    an electronic circuit mounted on the first stent electrode and electrically connected to the second stent electrode, wherein upon receipt of the radio frequency signal, the electronic circuit applies an electric defibrillation pulse between the first stent electrode and the second stent electrode.

2. The apparatus as recited in claim 1 wherein the electronic circuit comprises:
    an antenna for receiving the radio frequency signal;
    a detector connected to the antenna and tuned to the given frequency of the radio frequency signal and;
    an electrical storage device connected to the detector and storing electrical energy from the radio frequency signal; and
    a discharge circuit which applies electrical energy from the electrical storage device to the first stent electrode and the second stent electrode.

3. The apparatus as recited in claim 2 wherein the electrical storage device is a capacitor.

4. The apparatus as recited in claim 1 wherein the electronic circuit comprises:
    an antenna for receiving the radio frequency signal;
    a detector connected to the antenna and tuned to the given frequency of the radio frequency signal and;
    a capacitor;
    a charging circuit connected to the detector and the capacitor, and applying electrical energy derived from the radio frequency signal to produce a voltage across the capacitor; and
    a discharge circuit which applies the voltage across the capacitor to the first stent electrode and the second stent electrode.

5. The apparatus as recited in claim 1 wherein the first stent electrode is expandable within the blood vessel from a first cross-sectional size to a second cross-sectional size.

6. The apparatus as recited in claim 1 wherein the second stent electrode is expandable within the blood vessel from a first cross-sectional size to a second cross-sectional size.

7. The apparatus as recited in claim 1 further comprising a third electrode for implantation into a blood vessel in the medical patient and connected to the electronic circuit, wherein the electric defibrillation pulse also is applied across the first stent electrode and the third stent electrode.

8. A cardiac defibrillator, for a medical patient, comprising:
    a fibrillation detector, which determines when the medical patient requires defibrillation and produces a control signal;
    a transmitter connected to the fibrillation detector to produce a radio frequency signal and to transmit the control signal;
    a first stent electrode for implantation into a blood vessel at a first location in the medical patient;
    a second stent electrode for implantation into a blood vessel at a second location in the medical patient; and
    an electronic circuit mounted on the first stent electrode for placement within the blood vessel and electrically connected to the second stent electrode, the electronic circuit storing energy received from the radio frequency signal and in response to the control signal employing the stored energy to apply an electric defibrillation pulse across the first stent electrode and the second stent electrode.

9. The apparatus as recited in claim 8 further comprising a third electrode for implantation into a blood vessel in the medical patient with connection to the electronic circuit, wherein the electric defibrillation pulse also is applied across the first stent electrode and the third stent electrode.

10. The apparatus as recited in claim 8 wherein the electronic circuit comprises:

a detector tuned to the given frequency of the radio frequency signal;

a capacitor;

a charging circuit connected to the detector and the capacitor, and applying electrical energy derived from the radio frequency signal to produce a voltage across the capacitor; and a discharge circuit which in response to the control signal applies the voltage across the capacitor to the first stent electrode and the second stent electrode.

11. A method for defibrillation a heart of a medical patient, the method comprising:

implanting a first stent electrode into a blood vessel at a first location in the medical patient, the first stent electrode having an electronic circuit mounted thereon;

implanting a second stent electrode into a blood vessel at a second location in the medical patient, wherein second stent electrode is connected to the electronic circuit of the first stent electrode;

detecting when defibrillation of the heart is required;

in response to detecting when defibrillation of the heart is required, transmitting a wireless signal to the electronic circuit of the first stent electrode; and in response to receipt of the wireless signal, the electronic circuit applying a voltage across the first stent electrode and the second stent electrode.

12. The method as recited in claim 11 further comprising:

charging a capacitor using energy from the wireless signal; and discharging the capacitor to apply voltage across the first stent electrode and the second stent electrode.

* * * * *

UNITED STATES PATENT AND TRADEMARK OFFICE
CERTIFICATE OF CORRECTION

PATENT NO. : 6,907,285 B2  
DATED : June 14, 2005  
INVENTOR(S) : Stephen Denker et al.

It is certified that error appears in the above-identified patent and that said Letters Patent is hereby corrected as shown below:

<u>Title page, Item [54] and Column 1, line 1,</u>
Title, change "DEFIBRILLARTOR" to -- DEFIBRILLATOR --.

<u>Column 7,</u>
Line 16, change "defibrillation" to -- defibrillating --.

Signed and Sealed this

Sixteenth Day of August, 2005

JON W. DUDAS  
*Director of the United States Patent and Trademark Office*